United States Patent
Spargias

(10) Patent No.: US 8,187,223 B2
(45) Date of Patent: May 29, 2012

(54) ANTI-RESTENOSIS DRUG COVERED AND ELUTING BALLOONS FOR VALVULOPLASTY OF AORTIC VALVE STENOSIS FOR THE PREVENTION OF RESTENOSIS

(75) Inventor: Konstantinos Spargias, Attikis (GR)

(73) Assignee: EuroCor GmbH, Bonn (DE)

( * ) Notice: Subject to any disclaimer, the term of this patent is extended or adjusted under 35 U.S.C. 154(b) by 0 days.

(21) Appl. No.: 12/599,933

(22) PCT Filed: May 13, 2008

(86) PCT No.: PCT/GR2008/000035
§ 371 (c)(1),
(2), (4) Date: Oct. 12, 2010

(87) PCT Pub. No.: WO2008/139232
PCT Pub. Date: Nov. 20, 2008

(65) Prior Publication Data
US 2011/0021985 A1    Jan. 27, 2011

(30) Foreign Application Priority Data
May 14, 2007  (GR) .............................. 20070100291

(51) Int. Cl.
*A61M 31/00*    (2006.01)
(52) U.S. Cl. ............ 604/103.02; 604/103.07; 604/96.01
(58) Field of Classification Search ............... 604/96.01, 604/103.01, 103.02, 103.07, 103.08; 606/194
See application file for complete search history.

(56) References Cited

U.S. PATENT DOCUMENTS

| | | | |
|---|---|---|---|
| 6,682,545 B1 | 1/2004 | Kester | |
| 7,744,620 B2 | 6/2010 | Pedersen et al. | |
| 2004/0097804 A1 | 5/2004 | Sobe | |
| 2005/0090846 A1* | 4/2005 | Pedersen et al. | 606/159 |
| 2006/0280858 A1* | 12/2006 | Kokish | 427/2.1 |
| 2008/0021385 A1 | 1/2008 | Barry et al. | |

OTHER PUBLICATIONS

International Search Report for PCT Application No. PCT/GR2008/000035.

* cited by examiner

*Primary Examiner* — Laura Bouchelle
(74) *Attorney, Agent, or Firm* — Meyertons, Hood, Kivlin, Kowert & Goetzel, P.C.; Eric B. Meyertons

(57) ABSTRACT

In one embodiment, balloons are intended for use in valvuloplasty of stenosed aortic valves, with a potential use for valvuloplasty of other heart valves as well. Their common special feature is that the entire or part of their external surface is covered by a drug that is eluted at the valve tissues during the balloon brief contact with them at the time of dilatation. The drug acts against the process of restenosis, which almost uniformly occurs after some time. The shape of the balloon can be the classical cylindrical or an hour-glass shape that facilitates targeted delivery of the drug at the valve tissues. Additional balloon shapes are described for usage after valvuloplasty is carried out in order to achieve targeted drug delivery in the upper or both surfaces of the leaflets, and for prolonged contact with the valve tissues without interruption of blood circulation. An advantage of the balloons is that the local delivery of the drug will significantly reduce the likelihood of restenosis. As a result the procedural benefits for the patient are sustained in the long term, and the procedure from alleviating progresses into end-therapy.

9 Claims, 6 Drawing Sheets

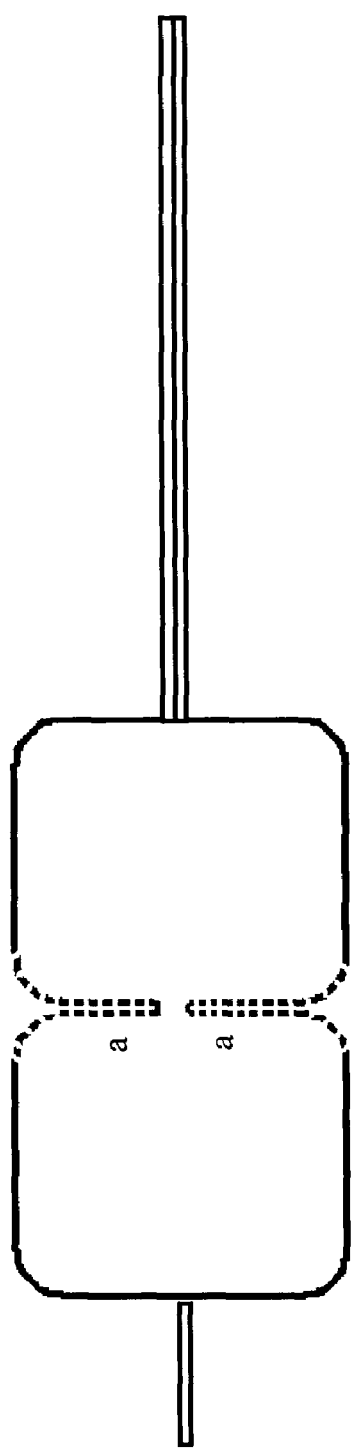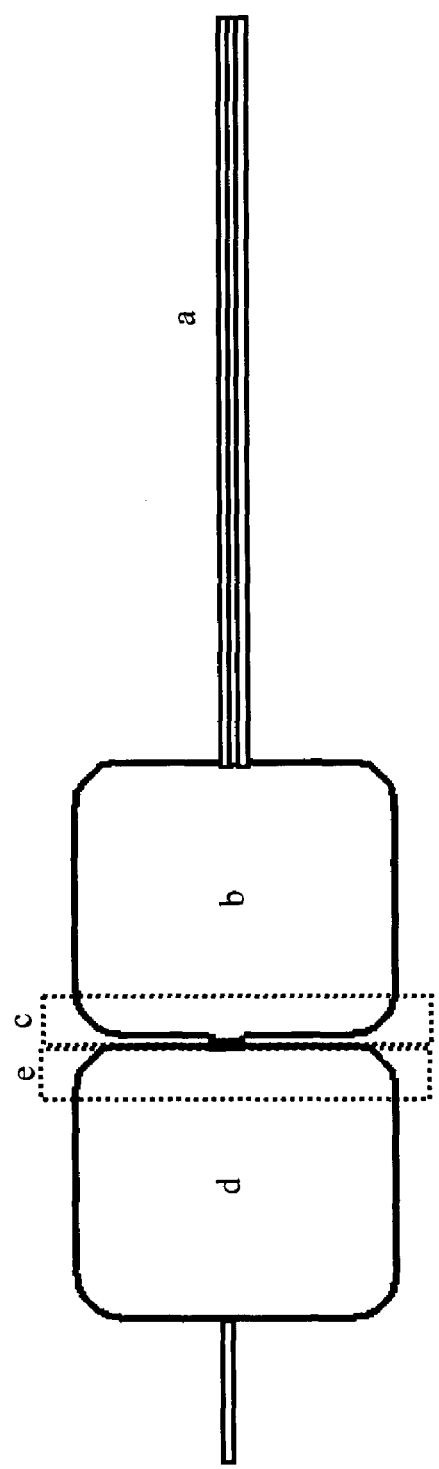
Figure 9
Figure 10

ANTI-RESTENOSIS DRUG COVERED AND ELUTING BALLOONS FOR VALVULOPLASTY OF AORTIC VALVE STENOSIS FOR THE PREVENTION OF RESTENOSIS

BACKGROUND OF THE INVENTION

1. Field of the Invention

The invention generally relates to the field of heart surgery. More particularly, the invention relates to the use of treated balloons in heart surgeries.

2. Description of the Relevant Art

Although aortic valve surgery is the gold standard, life saving treatment for symptomatic aortic stenosis, some patients do not undergo surgery. According to the 2003 Euro Heart Survey (lung B, et al, Eur Heart J 2003; 24: 1231-43) one third of community patients above the age of 75 with symptomatic severe aortic stenosis do not undergo surgery. The most apparent reason for this is the high mortality of the aortic valve replacement (AVR) in this population. The Medicare data in 2003 found a 8.8% in-hospital mortality of AVR in 145 000 patients aged over 65. There are other data showing average mortality of AVR up to 20% in octogenarians.

The incidence of known and severe aortic stenosis in US population in 2006 was 318,000 cases, of which only 74,000 had undergone AVR (based on Nkomo et al, Lancet 2006). According to other US estimates for 2006, of the 161,107 cases of ECHO diagnosed severe aortic stenosis over a 10-year period only 61,658 undergone AVR (based on Loma Linda data). Given the bad prognosis of severe symptomatic aortic stenosis, there has been an unmet need for another supplementary/alternative therapy.

Recently there has been considerable change in the technical approach to balloon aortic valvuloplasty (BAV) owing to the progress of percutaneous aortic valve implantation retrograde from the femoral artery and advances in the interventional hardware. A decrease in the complication rate of BAV over the past 15 years has been reported and has important implications regarding the morbidity associated with percutaneous aortic valve replacement techniques. In a recent series of 104 BAV procedures there were no procedural deaths and the incidence of total vascular complications was 9%. In-hospital, 1-, 2- and 3-year mortality rates were 6%, 44%, 62% and 71%, respectively. In the 1980's NHLB1 Balloon Valvuloplasty Registry the procedural mortality was 3% and the in-hospital mortality 11%.

BAV has been well demonstrated to moderately increase aortic valve area by an average of 0.3-0.4 $cm^2$ and reduce mean valvular gradient by roughly 50%. This is achieved despite the use of balloon diameters of 18-24 mm, not far smaller from the diameter of the aortic valve ring. Transient valve leaflet and annular stretch undoubtedly contribute to early recoil. The large majority of patients experience immediate symptomatic improvement.

However, the restenosis rates of 42-83% at 5-9 months and consistently >80% at 1 year remain the Achilles heel of the method and is the reason of the dismal long-term event-free and actuarial survival after balloon aortic valvuloplasty that resembles the natural history of untreated aortic stenosis.

It is now recognized that calcific aortic stenosis is a complex cellular process with features of atherosclerosis and biomineralization similar to osteogenesis, which should have specific pathways for targeted inhibition. Similarly, regulated processes may play a role in restenosis following BAV. Although the mechanisms of restenosis are poorly understood, scar formation and heterotopic ossification are believed to play a central role. If specific targeted inhibition of these processes is completely or even partially successful the long-term results of the BAV procedure will improve and it may become an acceptable treatment of aortic valve stenosis in the elderly.

An increasing number of patients are living into the 80s and beyond. Although many of these patients who may have symptomatic stenosis are acceptable candidates for surgical treatment, many are not. Given the uniform desire on behalf of the elderly for improvement in their quality of life, any advance in the BAV procedure that will limit restenosis and improve its long-term results would be welcome in this population.

The first effort to prevent restenosis following BAV was with radiation. The results of the RADAR pilot trial were published in Cathet Cardiovasc Intervent 2006; 68: 183-92. This was a series of 20 patients over 80 years of age with an estimated operative mortality risk above 15%. They underwent prophylactic external beam radiation therapy (EBRT) starting the day following the BAV procedure and for 3 days. A total dose of 1200 cGy and 1500-1800 cGy was administered in the low and high dose groups of patients. Restenosis was defined as over 50% late loss of acute gain in aortic valve area. By 1 year the restenosis rate in the low dose group was 30% and in the high dose group 11%, results impressively better than historical controls.

SUMMARY OF THE INVENTION

A balloon for use in valvuloplasty of aortic valve stenosis comprising a catheter having two lumens running through its entire shaft and reaching to its external end that remains outside of a patient's body. One lumen is used for the inflation of the balloon that is mounted to the other end of the catheter, and the other lumen is used for passing the guide-wire over which the balloon is advanced from the entry site to the application site. A drug against restenosis coats a portion of the external surface of the balloon. The antirestenotic drug is delivered from the external surface of the balloon to the aortic valve tissues during the inflation of the balloon in performing valvuloplasty.

BRIEF DESCRIPTION OF THE DRAWINGS

Advantages of the present invention will become apparent to those skilled in the art with the benefit of the following detailed description of embodiments and upon reference to the accompanying drawings in which:

FIG. 9 depicts a valvuloplasty balloon/catheter assembly, the balloon having a short and deep middle portion, the middle portion also having microholes/pores;

FIG. 10 depicts a valvuloplasty balloon/catheter assembly which is partially coated with an antirestenosis coating, the balloon having a middle portion that divides the balloon into two portions.

Figure 1:
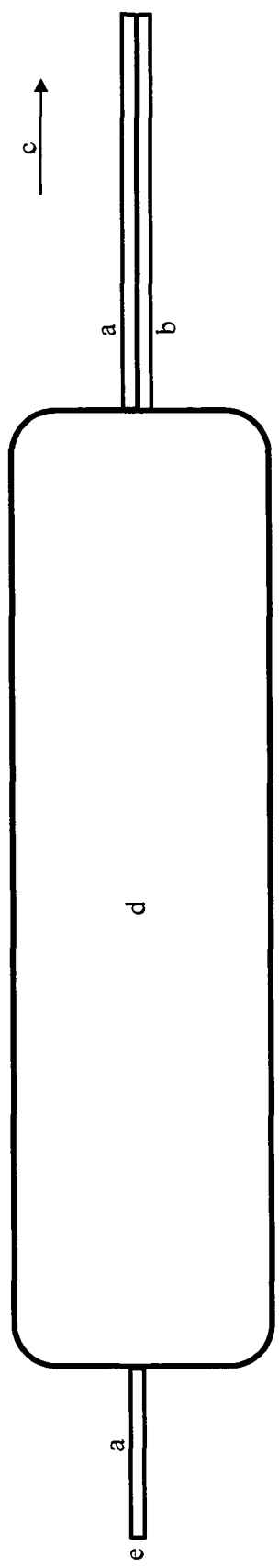
FIG. 1 depicts a valvuloplasty balloon/catheter assembly.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

The restenosis in coronary arteries and aortic valve following dilatation of a balloon share certain pathophysiological aspects. My hypothesis is that local antiproliferative drug delivery at the stenotic aortic valve with a balloon is a simple and effective way of preventing restenosis. If the restenosis problem is solved or even attenuated the acceptance/usage of this therapy would be completely revived.

I describe the development of drug-coated balloon for BAV, which elutes the loaded drug to the aortic valve tissues upon contact. There are numerous possibilities to drug coatings for this balloon, from drugs inhibiting scar formation to drugs inhibiting heterotopic ossification.

Since the mechanism of valve restenosis following BAY share certain characteristics with the coronary in-stent restenosis, drugs used for prevention of the latter can be tested for efficacy in the former. Paclitaxel for example is known to inhibit fibroblast migration in vitro and in vivo, and can be the first one to be used for coating a BAV balloon.

Recently, a pilot trial of external beam radiation therapy (EBRT) following BAV in 20 patients demonstrated a sustained significant improvement in the aortic valve area and mean gradient up to 1 year after the procedure (in reality there were only 2 outliers). However, this preventive strategy, even if it is conclusively proved, has certain inherent disadvantages such as the need for liaison with other medical specialties and medical facilities, precision of targeting, and prolonged hospital stay. The effort of restenosis prevention with radiation is reminiscent of the usage of brachytherapy for in-stent restenosis in coronary arteries, before the advent of drug-eluting stents.

In the event that antiproliferative drugs, such as paclitaxel, do not prove to be sufficiently effective, the component of valve restenosis due to heterotopic ossification could be dealt with incorporation in the coating of inhibitors of mineralization/calcification such as MGP, fetuin, osteopontinad and others or oral administration of inhibitors such as phosphate binding drugs (used by all chronic renal failure patients) and NSAA. (i.e. the selective cyclooxygenase-2 (COX-2) inhibitor Rofecoxib).

An effective drug-coated balloon for BAV would prevent restenosis with local drug delivery at the aortic valve leaflets at the time of balloon inflation. This method is obviously superior to EBRT, which requires prolonged hospital stay and considerable material and human resources.

If such a balloon proves to prevent restenosis and offers a long-term symptomatic improvement, it will undoubtedly become the treatment of choice in the elderly. The procedure will be much simpler, safer and cheaper compared to the implantation of a percutaneous prosthetic valve.

Even partial success with reduction and delay but not elimination of restenosis will be welcome, since repeat BAY can be done in those in need. It is known that repeat BAV is feasible, safe and offers further relief, but cannot be seen as the solution when the restenosis rate is close to 100% after 1 year. However, if the use of the drug-coated balloon attenuates and cuts down the restenosis to acceptable rates, BAV with drug-coated balloon will become readily acceptable.

DIOR (Eurocor, Germany) is a balloon catheter coated with paclitaxel (3 mcg/mm2 of balloon surface area) for use in the coronary arteries. It releases 35% of the drug with every 20-second contact with the vessel wall (i.e. 2 such dilatations release almost 70% of the loaded drug). It has been shown to significantly reduce late lumen loss and coronary in-stent restenosis compared with an uncoated balloon.

Figure 2:
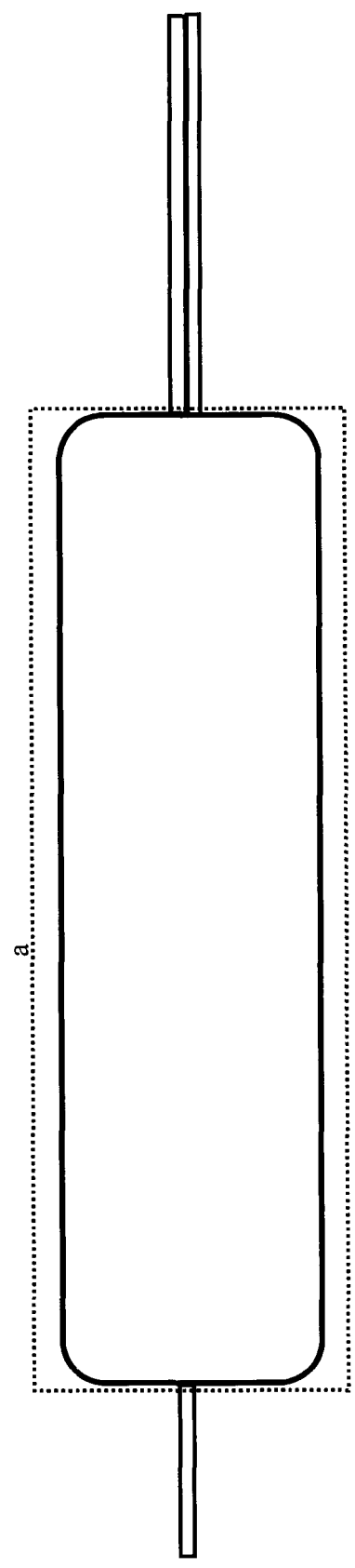
FIG. 2 depicts a valvuloplasty balloon/catheter assembly which includes an antirestenosis coating.

The aortic valvuloplasty balloon first introduced in the late 70s and today there are plenty plain valvuloplasty balloons manufacturers for use in heart valves. My proposal, which I submit for patenting, is an aortic valvuloplasty balloon that is covered by and elutes an antirestenosis substance (drug) to the aortic valve tissues upon contact with them during its inflation. A balloon for use in valvuloplasty of aortic valve stenosis includes the standard valvuloplasty balloon/catheter assemble (FIG. 1). The configuration of a catheter having 2 lumens (FIG. 1, *a,b*) running through its entire shaft and reaching to its external end (FIG. 1, *c*) that remains outside of the patient's body: one lumen is used for the inflation of the balloon (FIG. 1, *d*) that is mounted to the other end of the catheter (FIG. 1, *e*), and the other lumen is used for passing the guide-wire over which the balloon is advanced from the entry site to the application site. A drug against restenosis, which invariably occurs after valvuloplasty, coats the external surface of this balloon (FIG. 2, *a*). The antirestenotic drug is delivered from the external surface of the balloon to the aortic valve tissues during the inflation of the balloon in performing valvuloplasty. The drug is released to the aortic valve tissues and exerts its antirestenotic action. The same technology used in the aforementioned balloon catheter (DIOR) or any other drug-covering technology (mechanical or chemical bonding of the drug to the balloon surface) is applied in manufacturing of this balloon.

Figure 3:
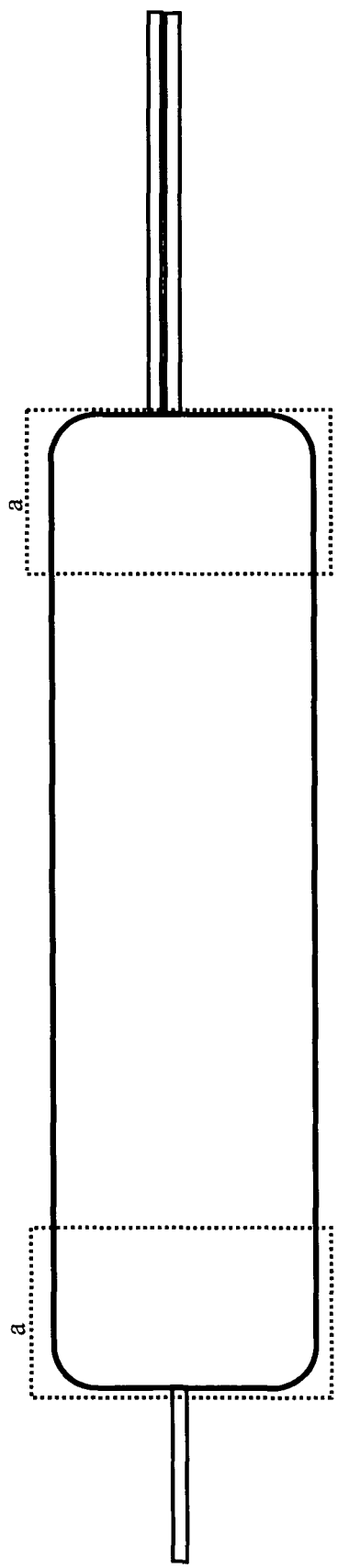
FIG. 3 depicts a valvuloplasty balloon/catheter assembly which is partially coated with an antirestenosis coating.

The entire external balloon surface or a part of it will be covered by the antirestenotic drug (e.g., the entire balloon surface is covered by drug FIG. 2). In another embodiment, the drug covers the middle-part area of the balloon that is coming into direct contact to the aortic valve and the edges remain uncovered as shown in FIG. 3, *a*. The other balloon surfaces at both ends remain uncoated.

The time of the balloon inflation in BAV cannot exceed 10-15 seconds, but multiple balloon inflations can be applied to reach a total time of balloon-valve contact of almost 1 minute. This allows the almost complete release of the loaded drug to the contacted tissue. If necessary, the quantity of the drug administered at the valve tissues by the balloon may be increased by storing higher dose of the drug at the balloon surface with appropriate technology (i.e. more and/or deeper and/or larger micropores).

A pilot trial in animals is designed to prove the concept of local drug delivery at the aortic leaflets followed by studies with experimental models of animal aortic valve stenosis and ultimately studies in humans with aortic valve stenosis.

This balloon will achieve contact and drug release at the inferior/external surfaces of the aortic valve, which have considerably larger area compared to the superior/internal surface for geometrical reasons.

The safety of drug delivery at other endothelial sites in the vicinity (i.e. aortic root and left ventricular outflow tract-LVOT) will be assessed. If animal or initial human experience raises concerns about possible side effects of paclitaxel or other drugs apposition at the aortic root/LVOT endothelium, a hour-glass shaped balloon, with its waist having a smaller diameter than that of its ends, is developed with the drug loaded only in the middle slimmer part (waist) of the balloon. With such a design the drug will be administered in a targeted manner at the aortic valve tissue only, and contact with other structures will be avoided. In addition, such a shape will act protectively with regards to any premature release of the drug into the blood flow.

Figure 4:
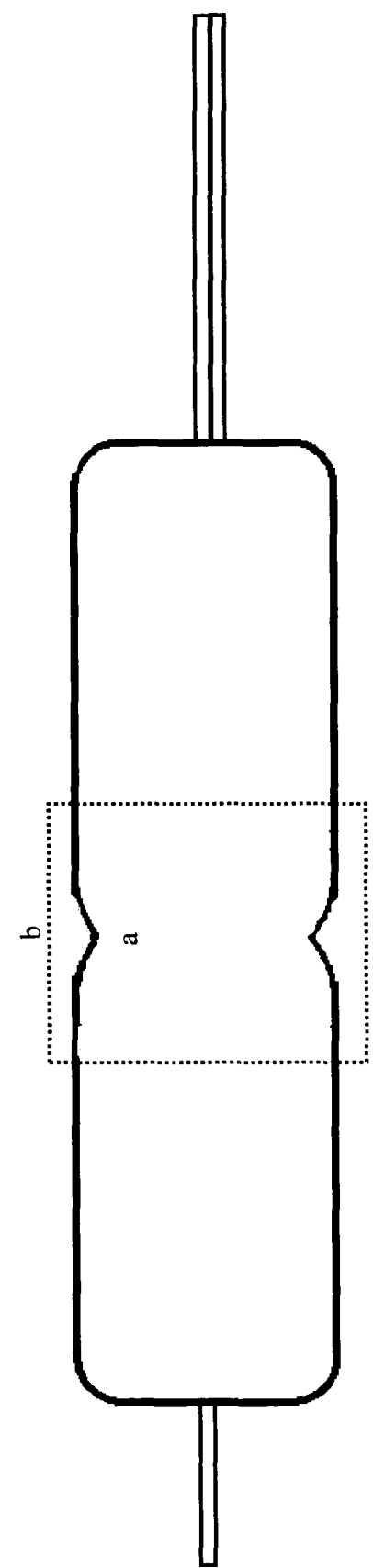
FIG. 4 depicts a valvuloplasty balloon/catheter assembly which is partially coated with an antirestenosis coating, the balloon having an hour-glass shape when inflated.
Figure 5:
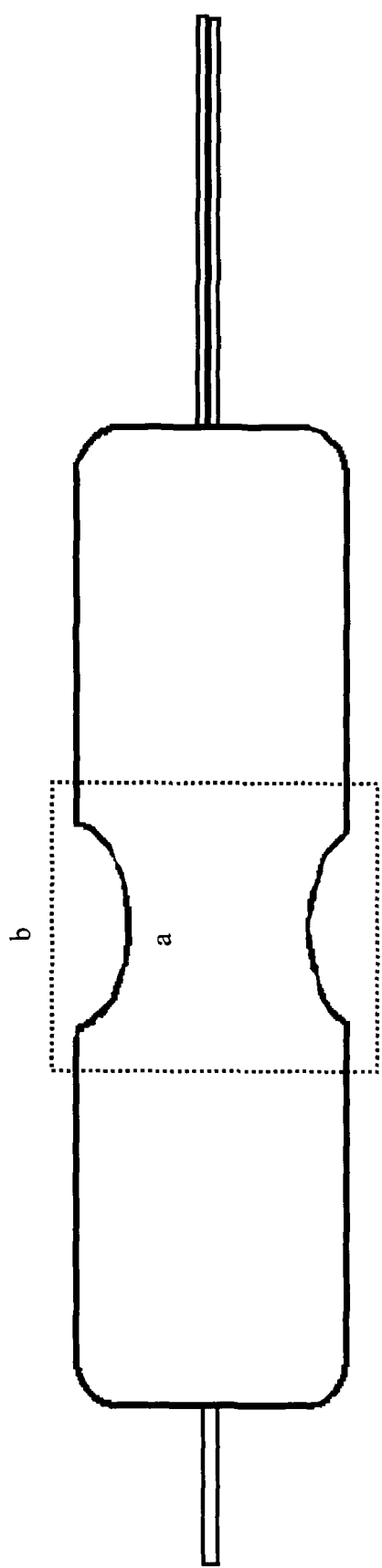
FIG. 5 depicts a valvuloplasty balloon/catheter assembly which is partially coated with an antirestenosis coating, the balloon having a concave middle portion when inflated.

FIG. 4 depicts a balloon that, when inflated, foams a circular crease at its middle part (FIG. 4, b), with only the surfaces of the middle part of this balloon are covered by the drug (FIG. 4, b). In BAV the pathological aortic valve contacts this balloon at the level of its drag-covered crease. FIG. 5 depicts a balloon similar to that of FIG. 4, one difference being that instead of forming a crease in the middle portion, a circular concave perimeter is formed (FIG. 5, b). Only the surfaces of the creased middle segment of this balloon are coated with an antirestenotic drug (FIG. 5, a).

All the previously described balloons achieve the opening of the stenotic aortic valve and contact and deliver their drug coating at the inferior/external surfaces of the aortic valve, which have considerably larger area compared to the superior/internal surface for geometrical reasons. In the event that delivery of the antirestenotic drug at the superior/internal surfaces of the aortic valve is desirable, two further BAV balloons have been developed to perform this task. These balloons cannot effectively dilate the stenotic aortic valve on their own, but they have been exclusively designed for drug delivery to prevent restenosis. BAV with a plain balloon or one of the balloons described in claims 1 to 6 should precede.

Figure 6:
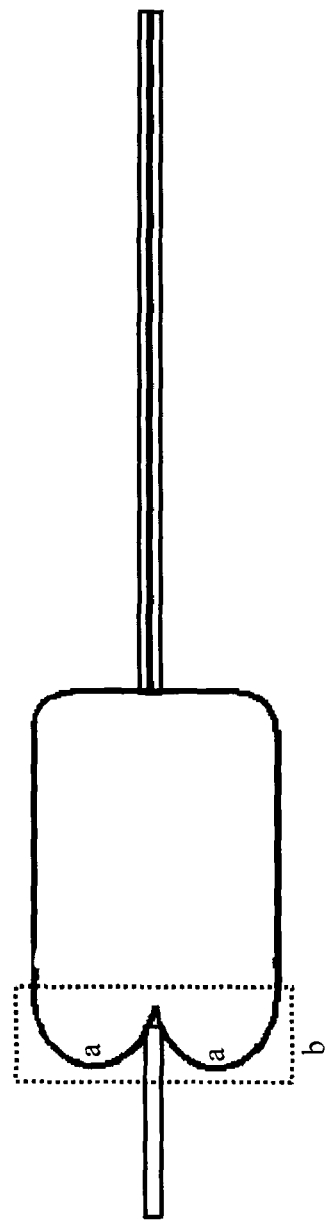
FIG. 6 depicts a valvuloplasty balloon/catheter assembly which is partially coated with an antirestenosis coating, the balloon having a distal end surface that has a shape that is the relief of the upper surfaces of the aortic valve leaflets.

FIG. 6 depicts the first of the aforementioned balloon invents, and is specifically designed to achieve delivery of the antirestenosis drug at the superior/internal surfaces of the aortic valve. This balloon is inflated within the aortic root and its distal surface, which is covered by the drug (FIG. 6, b), has a shape that is the relief of the upper surfaces of the aortic leaflets (FIG. 6, a). Then it is pushed against the upper surfaces of the leaflets and contacts them delivering drug upon contact.

Figure 7:
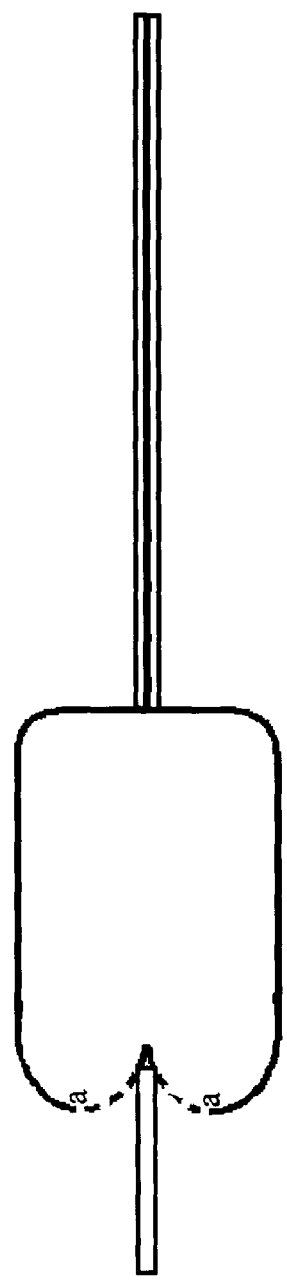
FIG. 7 depicts a valvuloplasty balloon/catheter assembly, the balloon having a distal end surface that has a shape that is the relief of the upper surfaces of the aortic valve leaflets, the end having microholes/pores.

FIG. 7 depicts a balloon that is a modification of that presented in FIG. 6. It is identical in shape but in addition it has micro-holes/pores at its distal edge surface that comes in direct contact with the upper aortic leaflet surfaces, allowing the fluid used for its inflation to exit the balloon and sprinkle or soak these surfaces. The inflating fluid is a dilution of the anti-restenosis drug and the size of the micro-holes is such that allows full balloon inflation at low pressures before the drug containing fluid starts exiting through them.

Figure 8:
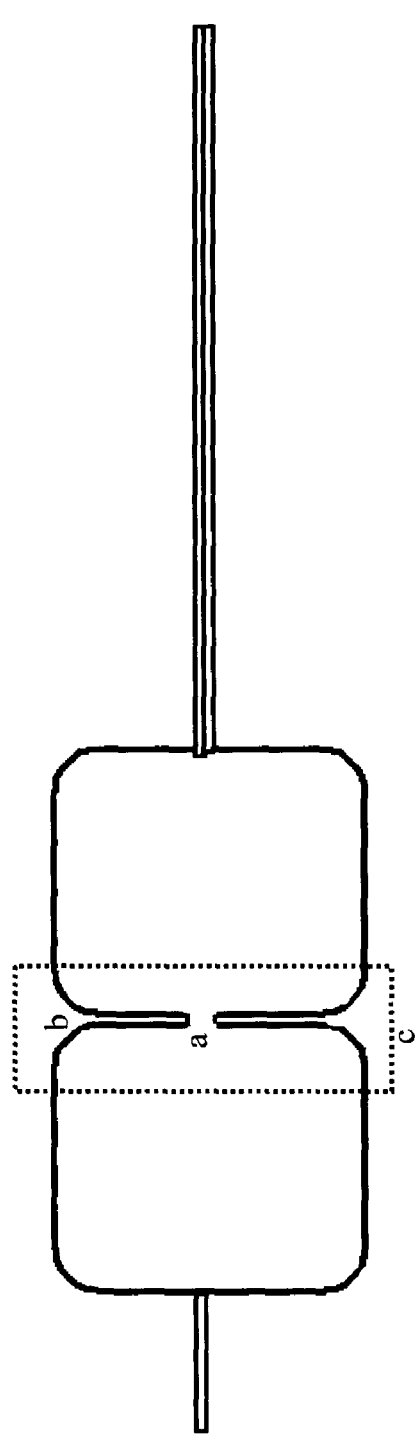
FIG. 8 depicts a valvuloplasty balloon/catheter assembly which is partially coated with an antirestenosis coating, the balloon having a short and deep middle portion.

FIG. 8 depicts the second of the aforementioned balloon invents. This balloon has been developed for the simultaneous delivery of the antirestenosis drug at both upper and lower surfaces of the aortic valve. When inflated the balloon has an hourglass shape with a very deep and narrow 'waist' (FIG. 8, b) that creates an 'envelope', in which the aortic valve leaflets are 'captured'. The surfaces of the balloon that form this 'envelope' are covered by the antirestenotic drug (FIG. 8, c) and its targeted delivery at both the upper and lower surfaces of the aortic leaflets is accomplished. In addition, such a shape acts protectively with regards to any premature release of the drug into the blood flow. The difference of this balloon design compared to that described by claims 4 to 6 lies to that the waist of the hour-glass (FIG. 8, a) is so narrow that when the balloon is inflated its lateral surfaces come into contact and so deep that it almost reaches the central long axis of the balloon. Because of its design this balloon is not indented for the initial opening of the stenotic aortic valve (that can be achieved with a plain balloon or one of the balloons described in claims 4 to 6) but it is used after its dilatation with another balloon for accomplishment of targeted drug delivery at both surfaces of the leaflets.

FIG. 9 depicts a balloon that is a modification of that presented in FIG. 8. It is identical in shape but in addition it has micro-holes/pores (FIG. 9, a) at its surface that forms the waist of the hour-glass and directly contacts the leaflets of the aortic valve. These micro-holes/pores allow the fluid used for the inflation of the balloon to exit the balloon and sprinkle or soak these surfaces. The inflating fluid is a dilution of the anti-restenosis drug and the size of the micro-holes is such that allows full balloon inflation at low pressures before the drug containing fluid starts exiting through them.

The balloons described in FIGS. 8 and 9 are in essence two-spaced balloons with the two spaces communicating at the 'neck' of the hour-glass they faun together and are inflated through a single lumen. Therefore, the simultaneous inflation of the two spaces of these balloons (the single inflation lumen of the catheter ends at the proximal balloon space and as a result this is inflated slightly ahead of the distal space) means that its precise positioning at the level of the aortic valve is of paramount importance if the leaflets of the valve are to be captured within the 'envelope' the two spaces of the balloon shape as it inflates. The surfaces of this envelope are covered with the antirestenotic drug (and/or have microholes/pores) that is delivered to both surfaces of the aortic leaflets. To avoid the need of the precise positioning another balloon has been developed and is depicted in FIG. 10. This balloon is similar to that described in FIG. 8, but the two spaces are in essence two different balloons in a row that do not communicate at the neck of the hour-glass and the distal space is inflated separately by an additional lumen. Therefore, the total number of the lumens in this system is three (FIG. 10, a): one is used for the advance of the system over the guide-wire, one is used for the inflation of the proximal and one for the inflation of the distal space. The advantage of this system is that the two in a row balloons that form the deep and narrow neck of the hour-glass can inflate separately allowing the 'dynamic' capture of the aortic valve between them. The proximal balloon is inflated first (FIG. 10, b) and the system is quickly pushed against the upper surfaces of the aortic leaflets delivering the drug coating it carries out at its distal surface (FIG. 10, c) to them. The inflation of the distal balloon (FIG. 10, d) follows immediately forming the 'envelope' that captures the aortic leaflets within. The proximal surface of the distal balloon is drug-coated (FIG. 10, e) and comes into contact with the lower surfaces of the aortic leaflets delivering the antirestenotic drug.

All the previously described balloons for use in BAV have a common disadvantage: they stop blood flow from the heart to the aorta and result in a circulation arrest during their inflation. This can be tolerated for very short time that cannot exceed 15-20 seconds. If a more prolonged contact with the drug covered balloon is required for an efficient delivery of the antirestenotic drug to the valve tissues the same or other drug-eluting balloon can be used for multiple short-lived inflations.

Figure 11:
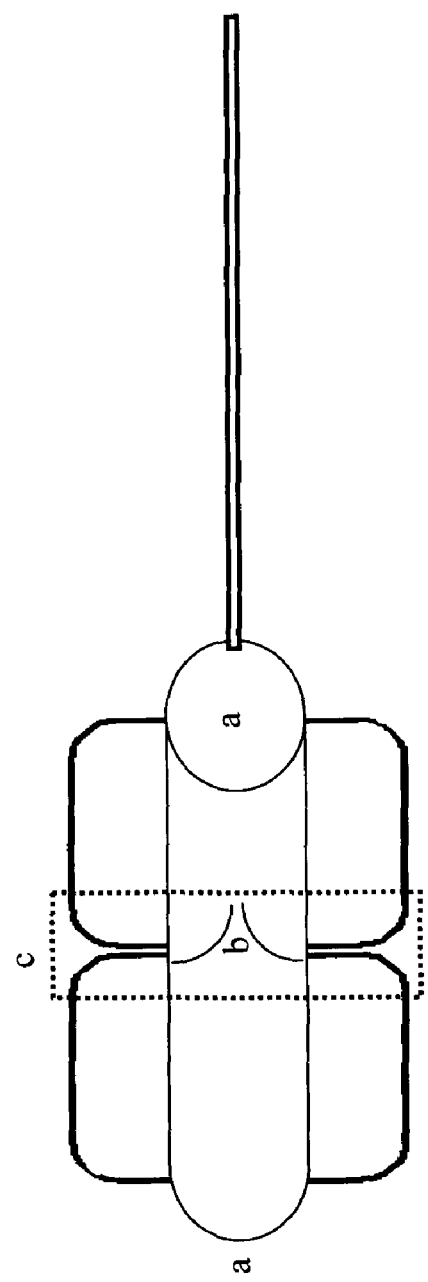
FIG. 11 depicts a valvuloplasty balloon/catheter assembly which is partially coated with an antirestenosis coating, the balloon having a middle portion that divides the balloon into two portions and a hollow center along its long axis that when the balloon is inflated it is expanded and creates a central cylindrical lumen.

Alternatively, a balloon system has been developed that can stay in contact with the aortic valve tissues for prolonged time allowing an effective cardiac output at the same time without halting the blood circulation from the heart to the aorta. FIG. 11 depicts an alternate balloon system. This is a balloon that is similar to that described in FIG. 8, but it has a hollow center along its long axis that when the balloon is inflated it is expanded and creates a central cylindrical lumen (FIG. 11, a) with an area of approximately 0.5-1.2 cm$^2$. In the internal surface of this lumen and at the level of the waist of the balloon there are 2 or 3 artificial crests (FIG. 11, b) that have the shape of the aortic leaflets. When the balloon is deflated and shrunk these crests are contained within the also shrunk central lumen of the balloon, but as the balloon is inflated the walls of the central cylindrical lumen are apposed and the lumen appears, the 'artificial' leaflets drop within it and function as a temporary 'artificial' aortic valve. As the hour-glass shaped balloon is inflated the aortic valve leaflets are captured within the envelope that is formed in the waist (as described in FIG. 8) and drug coating from the attendant balloon surfaces (FIG. 11, c) are delivered to the leaflet tissues. In addition, with the inflation and expansion of the balloon the central cylindrical lumen running its long axis from end to end opens allowing blood flow with each heart beat from the left ventricle to the aorta through the temporary 'artificial' aortic valve that drops and functions within the lumen. Backflow of the blood to the left ventricle is not possible through this 'artificial' valve. Competent cardiac function and output is preserved with the use of this balloon system allowing its prolonged inflation and contact with the aortic valve tissues and achieving this way release and delivery to the valve of larger quantities of the antirestenotic drug.

All previously described balloons can be used for valvuloplasty of other heart valves.

Phosphate binding drugs could be used for inhibition of the valve/vascular calcification component of restenosis in these studies.

Other antirestenotic and anticalcification drugs (alone or in combination) can be tested for local delivery with a coated balloon.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A balloon for use in valvuloplasty comprising a catheter having two lumens running through its entire shaft and reaching to its external end that remains outside of the patient's body: wherein one lumen is used for the inflation of the balloon that is mounted to the other end of the catheter, and the other lumen is used for passing a guide-wire over which the balloon is advanced from the entry site to the application site; wherein a drug against restenosis coats a portion of the external surface of the balloon; wherein the balloon has a shape of an hour-glass shape when inflated with its waist having a smaller diameter than that of its ends, wherein only the surfaces of the middle segment of this balloon are coated with the antirestenotic drug; and wherein the antirestenotic drug is delivered from the external surface of the balloon to the aortic valve tissues during the inflation of the balloon in performing valvuloplasty.

2. The balloon of claim 1, wherein the external balloon surface is partially coated with the antirestenotic drug at the level of its middle segment that contacts the aortic valve tissues upon inflation; and wherein the other balloon surfaces at both ends remain uncoated with the antirestenotic drug.

3. The balloon of claim 1, wherein the waist has a crease shape.

4. The balloon of claim 1, wherein the waist has a concave shape.

5. The balloon of claim 1, wherein the waist is has a shape such that, when it is inflated, the waist forms an envelope in which the aortic valve leaflets are captured during use; and wherein the surfaces of the envelope are coated with the antirestenotic drug that is delivered this way to both upper and lower surfaces of the aortic valve, which are inserted within.

6. The balloon of claim 5, wherein the surfaces that form the waist comprise microscopic holes/pores; wherein the microholes/pores allow the exit of an inflating solution when the balloon is expanded; and wherein the inflation solution comprises the antirestenotic drug that soaks both the upper and lower surfaces of the aortic leaflets.

7. The balloon of claim 5, wherein the waist reaches a central lumen of the system and separates completely the two spaces on its sides such that the two spaces do not communicate and the two spaces are inflated by two separate lumens.

8. The balloon of claim 5, comprising a hollow center along its long axis that, when the balloon is inflated, is expanded and creates a central cylindrical lumen.

9. The balloon of claim 1, wherein the balloon is designed for use in aortic valve stenosis.

* * * * *